US011286449B2

(12) United States Patent
Inui et al.

(10) Patent No.: US 11,286,449 B2
(45) Date of Patent: Mar. 29, 2022

(54) CELL CULTURE SUBSTRATUM, METHOD FOR PRODUCING CELL-CONTAINING MATERIAL, METHOD FOR PRODUCING CELL CULTURE SUBSTRATUM, METHOD FOR OBSERVING CELLS, AND CELL CULTURE SUBSTRATUM MAINTENANCE FLUID

(71) Applicants: Ohara Quartz CO., LTD., Wakayama (JP); NATIONAL UNIVERSITY CORPORATION NAGAOKA UNIVERSITY OF TECHNOLOGY, Nagaoka (JP); National Institute of Technology, Hachioji (JP)

(72) Inventors: Masahiko Inui, Wakayama (JP); Sunao Chatani, Wakayama (JP); Motohiro Tagaya, Nagaoka (JP); Satoshi Motozuka, Motosu (JP)

(73) Assignees: OHARA, INC., Kanagawa (JP); NATIONAL UNIVERSITY CORPORATION NAGAOKA UNIVERSITY OF TECHNOLOGY, Nagaoka (JP); NATIONAL INSTITUTE OF TECHNOLOGY, Hachioji (JP)

( * ) Notice: Subject to any disclaimer, the term of this patent is extended or adjusted under 35 U.S.C. 154(b) by 556 days.

(21) Appl. No.: 16/302,828

(22) PCT Filed: May 18, 2017

(86) PCT No.: PCT/JP2017/018725
§ 371 (c)(1),
(2) Date: Nov. 19, 2018

(87) PCT Pub. No.: WO2017/200055
PCT Pub. Date: Nov. 23, 2017

(65) Prior Publication Data
US 2019/0292504 A1    Sep. 26, 2019

(30) Foreign Application Priority Data
May 20, 2016 (JP) .............................. JP2016-101029

(51) Int. Cl.
*C12M 1/00* (2006.01)
*C12N 5/077* (2010.01)
(Continued)

(52) U.S. Cl.
CPC .............. *C12M 23/02* (2013.01); *C12M 3/00* (2013.01); *C12M 23/20* (2013.01); *C12N 1/00* (2013.01); *C12N 5/0654* (2013.01); *C12N 2533/00* (2013.01); *C12N 2533/10* (2013.01); *C12N 2533/14* (2013.01); *C12N 2535/00* (2013.01)

(58) Field of Classification Search
CPC .......... C12M 1/34; C12M 23/20; C12M 3/00; C12M 23/02; C12N 5/0068; C12N 1/00; C12N 5/0654; C12N 2533/10; C12N 2533/14; C12N 2533/12; C12N 2533/18; C12N 2533/00; C12N 2535/00
See application file for complete search history.

(56) References Cited

U.S. PATENT DOCUMENTS 5,018,847 A  5/1991  Ojima et al.
5,814,550 A  9/1998  Wolcott
(Continued)

FOREIGN PATENT DOCUMENTS

JP   H11513254 A   11/1999
JP   H02078444 A   3/2003
(Continued)

OTHER PUBLICATIONS

Sharpe et al. Differential Sensitivity to Trypsin of Human Bone-Derived Cells in Culture: Surface Changes Detected by Partitioning in Aqueous Two-Phase Systems. Cell Biochemistry and Function (1986), 4, 47-54. (Year: 1986).*
Invitrogen technical manual B-084243 0110, "Cell Culture Basics" (2010), 56 pages. (Year: 2010).*
Standard Operating Procedures # 1006.5, "Autoclave Sterilization" (2014), 3 pages. (Year: 2014).*
E. Cavalcanti-Adam et al., "Lateral spacing of integrin ligands influences cell spreading and focal adhesion assembly," European Journal of Cell Biology 85 (2006) pp. 219-224.
International Search Report corresponding to Application No. PCT/JP2017/018725; dated Aug. 8, 2017.
EP Extended Search Report corresponding to EP17799479.5 dated Jan. 3, 2020.
(Continued)

Primary Examiner — Sean C. Barron
(74) Attorney, Agent, or Firm — Cantor Colburn LLP

(57) ABSTRACT

The purpose of the present invention is to provide a cell culture substratum which has excellent resistance to liquid culture media and low cytotoxicity, can achieve a high cell adhesion ratio and a high viability of cultured cells, has excellent thermal stability, and is less likely to absorbs ultraviolet ray. A cell culture substratum which is provided with a substrate made from an inorganic material and has multiple concavo-convex structures on a culturing surface thereof, wherein, when the concavo-convex structures are measured with an atomic force microscope in accordance with JISB0601 and JISR1683 (measured area: a 1 μm-square, cut-off value of a low-pass contour curve filter: 1 nm, cut-off value of a high-pass contour curve filter: 170 nm), the average of the lengths of contour curve elements of the concavo-convex structures is 1 to 170 nm as measured in at least one direction (when a curve showing long-wavelength components that are blocked by the high-pass contour curve filter is converted to a straight line by the least square method, the average line is a line that is parallel with the straight line and indicates a height cumulative relative frequency distribution in the contour curve of 50%).

14 Claims, 6 Drawing Sheets

(51) Int. Cl.
*C12M 3/00* (2006.01)
*C12N 1/00* (2006.01)

(56) References Cited

U.S. PATENT DOCUMENTS

| | | |
|---|---|---|
| 2003/0162287 A1 | 8/2003 | Yamamoto et al. |
| 2007/0122901 A1* | 5/2007 | Morita ............... C12N 5/0068 435/325 |
| 2008/0213851 A1 | 9/2008 | Muller et al. |
| 2014/0220306 A1* | 8/2014 | Uchida ............... G02B 1/118 428/172 |
| 2016/0327695 A1 | 11/2016 | Masuyama et al. |

FOREIGN PATENT DOCUMENTS

| | | | |
|---|---|---|---|
| JP | 2003310256 A | | 11/2003 |
| JP | 2007076089 A | * | 3/2007 |
| JP | 2007535320 A | | 12/2007 |
| JP | 2012249547 A | | 12/2012 |
| JP | 2013039071 A | | 2/2013 |
| JP | 2013102713 A | | 5/2013 |
| JP | 2013244483 A | | 12/2013 |
| JP | 2013255483 A | | 12/2013 |
| JP | 2015062400 A | | 4/2015 |
| WO | 2005038011 A1 | | 4/2005 |
| WO | 2008042640 A1 | | 4/2008 |
| WO | 2015104968 A1 | | 7/2015 |

OTHER PUBLICATIONS

JPO Notification of Reasons for Refusal for corresponding JP Patent Application No. 2016-101029 dated Mar. 17, 2020.

Jung Yul Lim et al, "Cell Sensing and Response to Micro- and Nanostructured Surfaces Produced by Chemical and Topographic Patterning", Tissue Engineering, vol. 13, No. 8, pp. 1879-1891, XP055653422. Dated: (Aug. 1, 2007).

Clark P et al, "Cell guidance by ultrafine topography in vitro", Journal of Cell Science, vol. 99, No. 1, pp. 73-77, XP009162066. Dated: (May 1, 1991).

Ranella a et al, "Tuning cell adhesion by controlling the roughness and wettability of 3D micro/nano silicon structures", ACTA Biomaterialia, Elsevier, Amsterdam, NL, vol. 6, No., pp. 2711-2720, XP027052704. Dated: (Jul. 1, 2010).

Lucie Bacakova et al, "Polishing and coating carbon fiber-reinforced carbon composites with a carbor-titanium layer enhances adhesion and growth of osteoblast-like MG63 cells and vascular smooth muscle cellsin vitro, "Journal of Biomedical Materials Research, vol. 54, No. 4, pp. 567-578, XP055653266. Dated: (Jan. 1, 2000).

Agrawal a a et al, "Porous nanocrystalline silicon membranes as highly permeable and molecularly thin substrates for cell culture", Biomaterials, Elsevier Science Publishers BV., Barking, GB, vol. 31, No. 20, pp. 5408-5417, XP009150295: Dated: (Jul. 1, 2010).

Kazunori Shimizu et al, "Alignment of skeletal muscle myoblasts and myotubes using linear micropatterned surfaces ground with abrasives", Biotechnology and Bioengineering, vol. 103, No. 3, pp. 631-638, XP055653423. Dated: (Jun. 15, 2009).

* cited by examiner

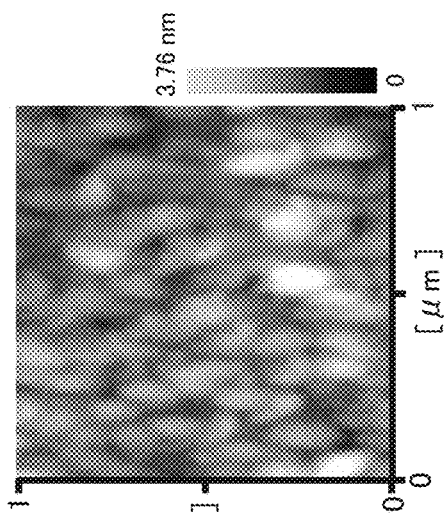
FIG. 3A
FIG. 3B
FIG. 3C
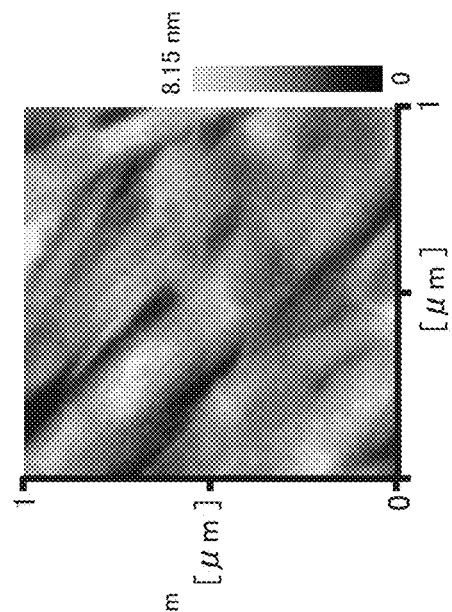
FIG. 3D
FIG. 3E

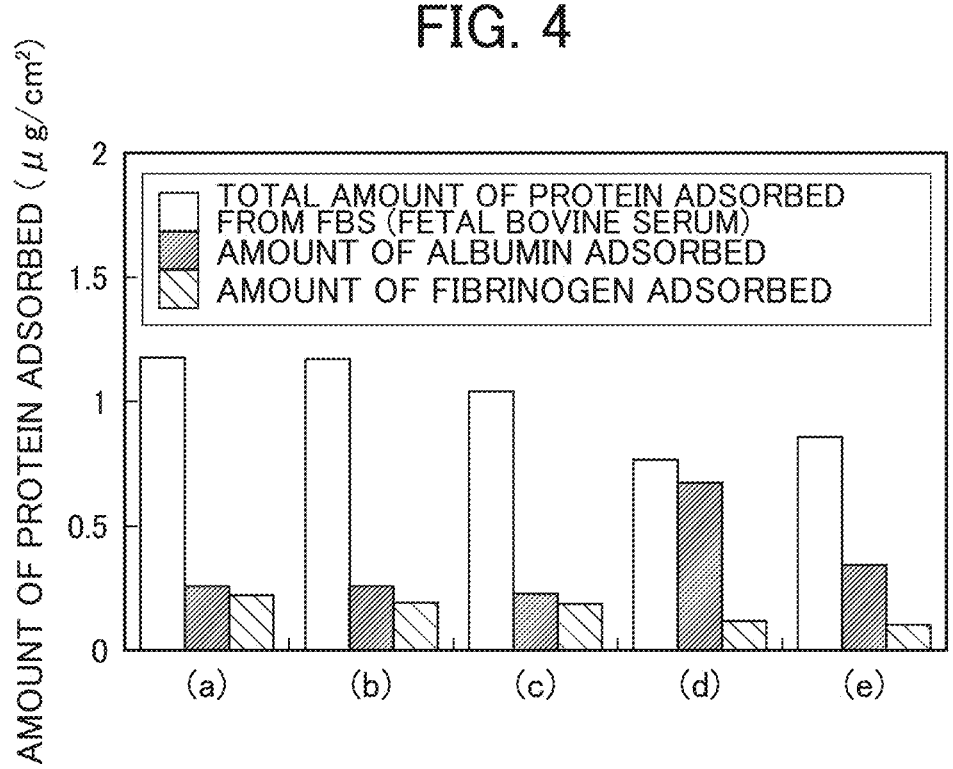

CELL CULTURE SUBSTRATUM, METHOD FOR PRODUCING CELL-CONTAINING MATERIAL, METHOD FOR PRODUCING CELL CULTURE SUBSTRATUM, METHOD FOR OBSERVING CELLS, AND CELL CULTURE SUBSTRATUM MAINTENANCE FLUID

CROSS REFERENCE TO RELATED APPLICATIONS

This is the U.S. national stage of application No. PCT/JP2017/018725, filed on May 18, 2017. Priority under 35 U.S.C. § 119(a) and 35 U.S.C. § 365(b) is claimed from Japanese Application No. 2016-101029, filed on May 20, 2016, the disclosure of which is also incorporated herein by reference.

TECHNICAL FIELD

The present invention relates to a cell culture substratum, a method for producing a cell-containing material, a method for producing a cell culture substratum, a method for observing cells, and a cell culture substratum maintenance fluid.

BACKGROUND ART

In recent years, regenerative medicine technology that involves implanting cellular tissue obtained by culturing cells in vitro into a body is gathering attention. For example, development of regenerative medicine technology for regeneration of stem cells such as iPS cells and biological tissues such as bone, blood vessels, skin, and heart through culturing of various cells that differentiate into biological tissues in cell culture dishes, is underway.

As a substratum to be used for culturing cells, a polystyrene cell culture dish has generally been used. However, the use of such a polystyrene cell culture dish as a culture substratum is problematic in that the cell adhesion rate of and the cell viability of cultured cells are low. Furthermore, the polystyrene cell culture dish is problematic in that it cannot be recycled via heat sterilization because of its low heat resistance.

Patent document 1 describes a cell culture apparatus, in which the substrate surface for culturing cells is coated with a colloidal silica film, as a result of focusing on the fact that such a polystyrene cell culture dish is not adequate for applications such as primary cell culture and serum-free cell culture.

Patent document 2 describes a method for preparing a bioactive surface by subjecting molecules or molecular aggregates on a surface having amorphous silicon dioxide (silica) to enzymatic modification, and specifically describes the use of polypeptide for enzymatic modification and employment of the method for cell culture.

Patent document 3 describes a cell culture substratum containing a copolymer of methoxyethyl acrylate and dimethylacrylamide, and one or more types of inorganic materials selected from water swelling clay minerals and silica.

Patent document 4 describes as a cell culture substratum with which a cell cluster (spheroid) formed via three-dimensional aggregation of cells can be cultured to have a uniform size without the use of any additive such as collagen gel, a cell culture substratum having a structure, in which multiple recessed parts having depths ranging from 100 μm to 500 μm and inner diameters ranging from 100 μm to 1000 μm are formed on the surface of the substratum. Patent document 4 also describes that the cell culture substratum has continuous concavo-convex structures, in which the most frequent pitch ranges from 2 nm to 10 μm.

Patent document 5 describes a cell culture substratum comprising, as a structure suitable for improving agglomeration efficiency, multiple recesses having funnel-shaped openings and micropores on the bottom are arranged on one surface of a glass substrate, as a result of focusing on the origin of the formation of a cell agglomerate (spheroid) and the extension of the cell agglomerate, wherein recesses are formed through a process flow comprising at least a glass substrate washing step, a Cr film mask-forming step, a resist mask-forming step, a Cr film mask opening-forming step involving etching, and a wet etching step for etching a glass substrate.

Non-patent document 1 describes that on the surface of a substratum of gold nanodot/polyethylene glycol, when the spacing between a gold nanodot and another gold nanodot is 58 nm rather than 110 nm, cell culture properties are more favorable.

Patent Document 1: Japanese Unexamined Patent Application (Translation of PCT Application), Publication No. H11-513254

Patent Document 2: Japanese Unexamined Patent Application (Translation of PCT Application), Publication No. 2007-535320

Patent Document 3: Japanese Unexamined Patent Application, Publication No. 2013-102713

Patent Document 4: Japanese Unexamined Patent Application, Publication No. 2012-249547

Patent Document 5: Japanese Unexamined Patent Application, Publication No. 2013-39071

Non-Patent Document 1: Cavalcanti-Adam, E. A.; Micoulet, A.; Blummel, J., Auernheimer, J.; Kessler, H.; Spatz, J. P., Eur, J. Cell Biol. 85 (2006) 219-224.

DISCLOSURE OF THE INVENTION

Problems to be Solved by the Invention

As described above, research and development on a cell culture substratum as an alternative to a polystyrene cell culture dish is underway. For example, a polystyrene cell culture dish is coated with an inorganic material as a cell culture substratum, making it possible to culture cells with its good resistance to liquid culture media and without being toxic to cells. However, the cell adhesion rate, the viability, and the thermal stability of cultured cells are yet to be improved, and there is a problem of ultraviolet rays absorption because of polystyrene used as a substrate material.

The purpose of the present invention is to provide a cell culture substratum which has excellent resistance to liquid culture media and low cytotoxicity, high cell adhesion rate and high cell viability of cultured cells, and excellent thermal stability, and is less likely to absorb ultraviolet rays. Moreover, another purpose of the present invention is to provide a method for producing a cell-containing material using the cell culture substratum, a method for producing the cell culture substratum, a method for observing cells, and a cell culture substratum maintenance fluid.

Means for Solving the Problems

The present inventors have discovered as a result of intensive studies on the mechanism at the time of cell culture, that in order to improve cell adhesiveness to a cell culture substratum, and thus to realize increased activity of cell proliferation and the like: stabilization of integrin proteins in cell pseudopodia and extracellular matrix proteins such as fibrinogen, fibronectin, laminin, and vitronectin intervening between cells and a substratum on the culturing surface of the cell culture substratum, and specifically protein scaffold forming are important; and the formation of a concavo-convex structure capable of accommodating integrin proteins (several nanometers (nm) to several tens of nm) and extracellular matrix proteins (several nm to several tens of nm) such as fibrinogen and fibronectin to predetermined degrees on the culturing surface of the cell culture substratum can improve the cell adhesiveness and the cell viability.

Based on the above findings, the present inventors have completed the present invention as described in the following (1) to (16).

(1) A cell culture substratum provided with a substrate composed of an inorganic material, wherein
the cell culture substratum has multiple concavo-convex structures on a culturing surface thereof,
when the concavo-convex structures are measured with an atomic force microscope in accordance with JISB0601 and JISR1683 (measured area: a 1 μm-square, cut-off value of a low-pass contour curve filter: 1 nm, cut-off value of a high-pass contour curve filter: 170 nm), the average length of the contour curve elements of the concavo-convex structures ranges from 1 nm to 170 nm as measured in at least one direction (when a curve representing long-wavelength components that are blocked by the high-pass contour curve filter is converted to a straight line by the least square method, the average line is a line that is parallel with the straight line and indicates a height cumulative relative frequency distribution in the contour curve of 50%).
(2) The cell culture substratum according to claim 1, wherein the watershed height of the contour curve ranges from 0.1 nm to 8 nm (the watershed height is, under a condition where an upper end line indicating a height cumulative relative frequency distribution of 100% in the contour curve and a lower end line indicating a height cumulative relative frequency distribution of 0% are inverted for horizontal correction, the average distance between the lowest point of valleys after inversion and the lower end line in the contour curve measured by the watershed method).
(3) The cell culture substratum according to (1) or (2), wherein the aspect ratio of period W1 in the contour curve of the concavo-convex structures in direction X to period W2 in the contour curve of the concavo-convex structures in direction Y perpendicular to direction X is 1.95 or less (aspect ratio is the average found by dividing the value of period W1 or W2 higher than the other by the value of the same lower than the other).
(4) The cell culture substratum according to any one of (1) to (3), wherein the culturing surface forms the concavo-convex structures coated with a porous $SiO_2$ film.
(5) The cell culture substratum according to any one of (1) to (3), wherein the culturing surface forms the concavo-convex structures coated with a calcium phosphate compound film.
(6) The cell culture substratum according to (4) or (5), wherein the thickness of the porous $SiO_2$ film or the calcium phosphate compound film ranges from 1 nm to 200 nm.
(7) The cell culture substratum according to any one of (1) to (6), wherein the inorganic material contains $SiO_2$.
(8) The cell culture substratum according to any one of (1) to (7), wherein the culturing surface does not contain $B_2O_3$.
(9) The cell culture substratum according to any one of (1) to (8), wherein the visible-light transmission is 70% or more.
(10) The cell culture substratum according to any one of (1) to (9), wherein the concavo-convex structures are grooved, porous or flaky.
(11) A method for producing a cell-containing material, having a step of culturing cells using the cell culture substratum according to any one of (1) to (10).
(12) A method for producing a cell-containing material, comprising culturing cells using a cell culture substratum comprising polystyrene, wherein when the culture time required for the cell density to reach 90% of the culturing surface of the cell culture substratum comprising polystyrene is designated as 1T, cells are cultured with the culture time between ½T and ⅔T using the cell culture substratum according to any one of (1) to (10).
(13) A method for producing a cell culture substratum, comprising autoclaving the cell culture substratum according to any one of (1) to (10), and then producing the cell culture substratum for recycling.
(14) The method for producing the cell culture substratum according to (13), comprising removing proteins on the cell culture substratum after autoclaving.
(15) A method for observing cells, comprising optically observing cells on the cell culture substratum according to any one of (1) to (10).
(16) A maintenance fluid, which is used for removing a cell adhesive protein on the cell culture substratum according to any one of (1) to (10), and contains a component for degrading the cell adhesive protein.

Effects of the Invention

According to the present invention, a cell culture substratum having excellent resistance to liquid culture media, low cytotoxicity, and, high cell adhesion rate and high cell viability of cultured cells, excellent thermal stability, and being less likely to absorb ultraviolet rays can be provided. Furthermore, the present invention can provide a method for producing a cell-containing material using the cell culture substratum, a method for producing a cell culture substratum, a method for observing cells and a cell culture substratum maintenance fluid.

BRIEF DESCRIPTION OF THE DRAWINGS

FIG. 2A shows X-ray diffraction patterns of the low-angle region and FIG. 2B shows X-ray diffraction patterns of the high-angle region.

FIG. 3A TO FIG. 3E show atomic force microscopic images showing the concavo-convex structures of the culturing surfaces of the cell culture substrata of Examples 1 to 3 and Comparative examples 1 and 2.

FIG. 4 is a graph showing the amounts of proteins adsorbed on the culturing surfaces of the cell culture substrata of Examples 1 to 3 and Comparative examples 1 and 2.

PREFERRED MODE FOR CARRYING OUT THE INVENTION

Embodiments of the present invention are as described below. Further, the present invention is not to be interpreted as being limited by these examples.
(Cell Culture Substratum)

The cell culture substratum of the embodiments is provided with a substrate composed of an inorganic material and has multiple concavo-convex structures on the culturing surface. In the embodiments, when the concavo-convex structures are measured in accordance with JISB0601 (2013) and JISR1683 (2014) using an atomic force microscope (measured area: 1 μm-square, cut-off value of a low-pass contour curve filter: 1 nm, and cut-off value of a high-pass contour curve filter: 170 nm), the average length of the contour curve elements of the concavo-convex structures ranges from 1 to 170 nm as measured in at least one direction.

Upon measurement with an atomic force microscope, a direction, into which high-speed line scanning of the culturing surface of a cell culture substratum; that is a sample, is performed with a probe for measuring atomic force, is designated as direction A. Moreover, a direction, into which the starting point of high-speed line scanning with a probe is gradually moved perpendicular to direction A, is designated as direction B. The measured area of the culturing surface of the cell culture substratum is 1 μm-square; that is, an area of 1 μm into direction A×1 μm into direction B can be set. The number of measuring points may be 256 points into direction A, and 256 points into direction B. Furthermore, when measurement is performed minutely, the number of measuring points may be 512 points into direction A, and 512 points into direction B, and can be adequately adjusted depending on the size of the measured area, and the like. The cut-off value of a low-pass contour curve filter is set at 1 nm, and the cut-off value of a high-pass contour curve filter is set at 170 nm, so that the length "1 nm to 170 nm" of contour curve elements can be detected.

Figure 1:
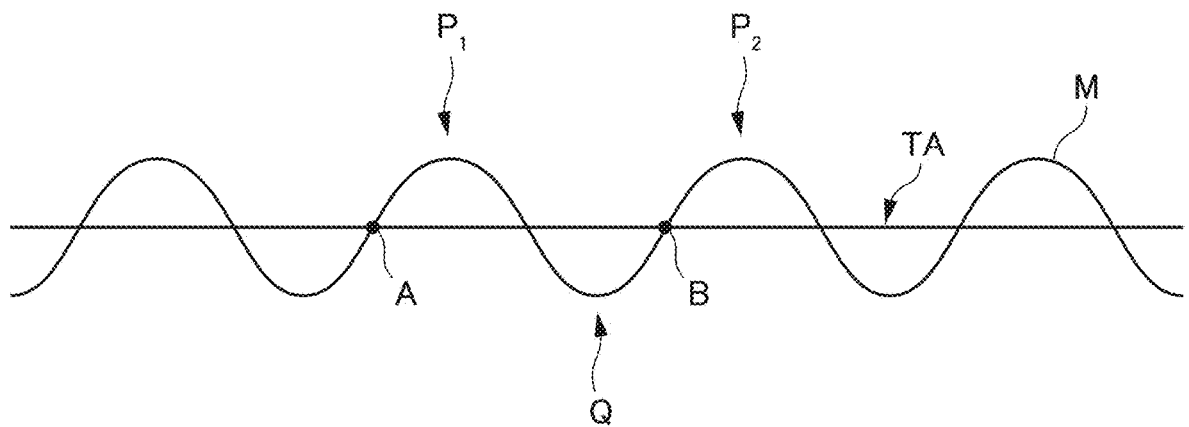
FIG. 1 is a schematic diagram showing an example of the contour curve of concavo-convex structures in an embodiment of the present invention.

The contour curve of concavo-convex structures can be obtained by measurement using an atomic force microscope. FIG. 1 is a schematic diagram showing an example of the contour curve of the concavo-convex structures in an embodiment. Portions above average line TA of contour curve M of the concavo-convex structures are referred to as peaks, and portions below the same are referred to as valleys. The average line in the present invention is a line that is parallel with a straight line and indicates a height cumulative relative frequency distribution in the contour curve of 50%, when a curve representing long wavelength components that are blocked by the high-pass contour curve filter is converted to the straight line by the least-squares method. Note that "height" with regard to cumulative relative frequency distribution refers to a difference between the value of the vertical coordinate axis at each point and the lowest value of the values of the vertical coordinate axis. As shown in FIG. 1, contour curve M in the present embodiments has multiple peaks and valleys, wherein a curve portion consisting of peak $P_1$, and valley Q adjacent thereto (specifically, on the right side of $P_1$) is one contour curve element, which is followed by peak $P_2$. Therefore, the length of such a contour curve element is the distance from starting point A of peak $P_1$ to end point B of valley Q adjacent to peak $P_1$. The present invention has at least one direction wherein the average length of the contour curve elements ranges from 1 nm to 170 nm.

Integrin proteins attached to cell pseudopodia and extracellular matrix proteins tend to be present every about 1 nm to 170 nm. Hence, with the average length of contour curve elements ranging from 1 nm to 170 nm, multiple integrin proteins and extracellular matrix proteins can be efficiently accommodated within recesses. The average length of contour curve elements ranges from preferably 1 nm to 130 nm, and further preferably 1 nm to 80 nm. In the culturing surface of the cell culture substratum of the present embodiments, measuring directions, by which the average length of contour curve elements is within the above preferable ranges, are preferably two or more directions. This tends to improve the accommodation of integrin proteins and extracellular matrix proteins, and cell adhesiveness. Measured areas, by which the average length of contour curve elements is within the above preferable ranges, are preferably multiple areas. Moreover, in the culturing surface of the cell culture substratum of the present embodiments, the existence probability of the measured areas, by which the average length of contour curve elements is within the above preferable ranges, is preferably 10% or more, more preferably 20% or more, and further preferably 30% or more.

The height of a contour curve is preferably optimized in view of cell adhesiveness to a culturing surface. Specifically, the watershed height of a contour curve ranges from preferably 0.1 nm to 8 nm, more preferably 1 nm to 6 nm, and further preferably 1 nm to 5 nm. This mechanism is assumed as follows. Extracellular matrix proteins (fibrinogen, fibronectin, vitronectin, and laminin) adsorb from a cell culture solution to a substratum before cell adhesion. Of these proteins, proteins important for cell binding and cell adhesion are fibrous proteins, the central portions of which are hydrophobic, and the terminal portions of which are electrostatically charged. Accordingly, fibrous proteins become most adsorbable to a substratum when the terminal portions are incorporated into the concavo-convex structures, but the central portions are not incorporated into the concavo-convex structures. Furthermore, when the density of fibrous proteins increases, hydrophobic interaction between exposed hydrophobic central portions causes the standing-up of fibrous protein molecules, and contact frequency between regions to which cells can bind and cells is increased, facilitating the binding of cells. Such synergistic action tends to result in an increased cell adhesion rate. Since the size of the terminal portion of an extracellular matrix protein (size after hydration) is several nm, the watershed height of a contour curve within the above ranges is considered to be preferred. The watershed height of a contour curve is, under conditions where the upper end line indicating a height cumulative relative frequency distribution in the contour curve of 100% and the lower end line indicating a height cumulative relative frequency distribution of 0% are inverted for horizontal correction, the average distance between the lowest point of valleys after inversion and the lower end line in a contour curve measured by the watershed method. In measurement by the watershed method, automatic processing is performed based on a program to which Vincent-Soille's algorithm (L. Vincent, P. Solle "Watersheds in Digital Spaces: An Efficient Algorithm Based on Immersion Simulations", IEEE Transactions on Pattern Analysis and Machine Intelligence, 13 (6), 583 (1991).) is applied.

Whereas in the concavo-convex structures of the present embodiments, the average length of contour curve elements as measured by the above measurement method ranges from 1 nm to 170 nm, recessed parts having inner diameters ranging from 100 μm to 1000 m, and depths ranging from 100 μm to 500 μm as described in patent document 4 above may be absent on the substratum of the present embodiments. In particular, the aspect of patent document 4 wherein a concavo-convex structure is formed on the inner surfaces of the recessed parts having inner diameters ranging from 100 μm to 1000 μm, and depths ranging from 100 μm to 500 μm is a structure for forming spheroids (cell clusters), and is preferably not included in the present embodiments that do not intend to form spheroids.

The concavo-convex structures are preferably grooved, porous or flaky concavo-convex structures. If the concavo-convex structures are grooved, porous or flaky concavo-convex structures, the structures can regularly accommodate proteins, and cells for adhesion can be regularly arranged on the culturing surface. Particularly in the case of porous concavo-convex structures, the charged terminal portions of extracellular matrix proteins closely adhere to the concavo-convex structures and surrounded, the above-described adsorption of extracellular matrix proteins to the substratum and standing-up of the extracellular matrix proteins tend to take place. Hence, the porous structures are advantageous in that the cell adhesion rate can be easily increased. Furthermore, for example, in the case of grooved concavo-convex structures, these structures can be prepared by shaving the surface of a substrate or a substratum. In the case of porous concavo-convex structures, the structures can be prepared by pressing members for forming pores from above the surface of a substrate or a substratum. These structures are also excellent in that the concavo-convex structures can be easily formed. In the present embodiments, the term "grooved" refers to a shape such that recesses are successively formed into the depth direction. Straight-line grooved structures are preferred in view of regularly accommodating proteins. Moreover, the term "porous" refers to a condition where pores are scattered over the substratum surface when the substratum is looked down from above. Furthermore, the term "flaky (concavo-convex structures)" refers to concavo-convex structures wherein recesses are present around projections. Such grooved, porous or flaky concavo-convex structures can be confirmed as an atomic force microscopic image.

In the present embodiments, the aspect ratio of average length W1 of contour curve elements of the concavo-convex structures in direction X (the direction satisfying that the average length of contour curve elements of the concavo-convex structures ranges from 1 nm to 170 nm) to average length W2 of contour curve elements of the concavo-convex structures in direction Y perpendicular to direction X is preferably 1.95 or less. The aspect ratio is the average found by dividing the value of W1 or W2 higher than the other by the value of W1 or W2 lower than the other. When the aspect ratio is 1.95 or less, the charged terminal portions of extracellular matrix proteins closely adhere to the concavo-convex structures and are surrounded, so that the above adsorption of extracellular matrix proteins to the substratum and standing-up of the extracellular matrix proteins tend to take place, and the cell adhesion rate can be easily increased. More preferably, the aspect ratio is 1.5 or less, and further preferably 1.2 or less. Moreover, when the values of average W1 and W2 are the same, the aspect ratio is 1 that is the lower limit.

A roughness value can also be used as an index representing the surface roughness of concavo-convex structures. Roughness value is a value produced by converting surface roughness into numbers using Root-mean-square value (Rrms). In the following equation, n is the number of measuring points (n=265×265), h(Xi) is the height at measuring point Xi, and h is the average value of heights. Rrms value is represented by the square root of the mean square of the deviation with respect to average value h.

$$R_{rms} = \sqrt{\frac{1}{n}\sum_{i=1}^{n}(h(x_i) - h)^2}$$

The present inventors hypothesize about the following mechanism of the property of cells to adhere to a culturing surface (cell adhesiveness). Specifically, the present inventors consider that when a cell culture solution is accommodated in a cell culture substratum, the following processes (1) to (3) proceed and thus cells exhibit functions.
(1) Ions and water are brought into contact with a culturing surface to form a hydration layer (first adsorption process).
(2) Proteins in the cell culture solution adsorb to the hydration layer on the culturing surface to form a protein-adsorbed layer (second adsorption process).
(3) Cells adhere to the protein-adsorbed layer for extension (third adhesion process). Furthermore, the present inventors consider that through accommodation of proteins (protein termini) in recesses of the concavo-convex structures of the culturing surface, cell adhesiveness and cell viability are improved.

<Culture Substratum>

Cell culture substrata are not particularly limited, as long as they are substrata provided with substrates composed of inorganic materials. Examples of inorganic materials include aluminum oxide, aluminium nitride, boron nitride, silicon nitride, silicon oxide, aluminum hydroxide, calcium hydroxide, calcium carbonate, calcite, calcium carbonate, light calcium carbonate, heavy calcium carbonate, ultrafine calcium carbonate, plaster, calcium sulfate, marble, barium sulfate, barium carbonate, magnesium oxide, magnesium carbonate, magnesium hydroxide, strontium carbonate, kaolin clay, calcined clay, talc, sericite, optical glass, and glass beads, and one type of these examples may be used individually or two or more types of the same may also be used in combination. Moreover, as an inorganic material, a calcium phosphate compound may also be used. A calcium phosphate compound is preferably a mixture or a mixed reactant of a phosphoric acid source (one or more types of salt selected from phosphoric acid, sodium primary phosphate, sodium secondary phosphate, potassium primary phosphate, potassium secondary phosphate, ammonium primary phosphate, ammonium secondary phosphate, and the like) and a calcium source (one or more types of salt selected from calcium nitrate, calcium carbonate, calcium chloride, calcium hydroxide, calcium acetate, and the like). Examples of the calcium phosphate compound include calcium monohydrogen phosphate anhydride ($CaHPO_4$), calcium monohydrogen phosphate dihydride ($CaHPO_4 \cdot 2H_2O$), tricalcium phosphate ($Ca_3(PO_4)_2$), calcium dihydrogen phosphate anhydride ($Ca(H_2PO_4)_2$), calcium dihydrogen phosphate hydride ($Ca(H_2PO_4)_2 \cdot H_2O$), tetracalcium phosphate ($Ca_4O(PO_4)_2$), hydroxyapatite ($Ca_{10}(PO_4)_6(OH)_2$), octacalcium phosphate ($Ca_8H_2(PO_4)_6 \cdot 5H_2O$), amorphous calcium phosphate ($Ca_3(PO_4)_2 \cdot nH_2O$). Of these examples, hydroxyapatite and octacalcium phosphate useful for cell culture are preferable, and a more preferable example is hydroxyapatite having high biocompatibility and high cell affinity. An inorganic material is preferably silicon oxide (silica) and more preferably quartz glass. The use of silica, an accessory bone component, makes it possible to highly activate culturing of osteoblasts. Moreover, the side part is preferably composed of the same inorganic material as of the substrate. Note that since an oxide of boron may affect a living body, a cell culture substratum preferably contains no $B_2O_3$ in its culturing surface. In addition, non-culturing surface(s) may or may not contain $B_2O_3$ as long as the culturing surface contains no $B_2O_3$. The use of a substrate composed of inorganic materials realizes a cell culture substratum having excellent thermal stability and resistance to liquid culture media, without being cytotoxic to cells. Furthermore, compared to a case in which polystyrene is used as a substrate material, the cell culture substratum is unlikely to absorb ultraviolet rays. Furthermore, even a cell culture substratum containing an inorganic material as in patent document 3, for example, is preferably not included in the cell culture substratum of the present embodiments, when it contains an organic compound such as a copolymer of methoxyethyl acrylate and dimethylacrylamide.

<Cells>

Examples of cells to be cultured on the cell culture substratum include, but are not particularly limited to, fat cells, osteoblasts, chondrocytes, skeletal muscle cells, myofibroblasts, hepatocytes, iPS cells, peripheral nerve cells, glial cells, pigment cells, corneal endothelial cells, keratocytes, iris parenchymal cells, trabecular cells, smooth muscle cells, chondrocytes, osteocytes, fat cells, endocrine cells, chromaffin cells, vascular smooth muscle cells, hair matrix cells, chondrocytes, amnion derived cells, and fetal kidney derived cells.

<Film>

The culturing surface of the cell culture substratum preferably forms concavo-convex structures coated with a porous $SiO_2$ film. Coating with the porous $SiO_2$ film tends to be able to highly activate cell culturing.

The culturing surface of the cell culture substratum also preferably forms concavo-convex structures coated with a calcium phosphate compound film. Coating with the calcium phosphate compound film tends to be able to highly activate cell culturing such as improved cell viability upon culturing over a prolonged period, and increased cell area. The calcium phosphate compound is preferably a mixture or a mixed reactant of a phosphoric acid source (one or more types of salt selected from phosphoric acid, sodium primary phosphate, sodium secondary phosphate, potassium primary phosphate, potassium secondary phosphate, ammonium primary phosphate, ammonium secondary phosphate, and the like) and a calcium source (one or more types of salt selected from calcium nitrate, calcium carbonate, calcium chloride, calcium hydroxide, calcium acetate, and the like). Examples of the calcium phosphate compound include calcium monohydrogen phosphate anhydride ($CaHPO_4$), calcium monohydrogen phosphate dihydrate ($CaHPO_4 \cdot 2H_2O$), tricalcium phosphate ($Ca_3(PO_4)_2$), calcium dihydrogen phosphate anhydride ($Ca(H_2PO_4)_2$), calcium dihydrogen phosphate hydride ($Ca(H_2PO_4)_2 \cdot H_2O$), tetracalcium phosphate ($Ca_4O(PO_4)_2$), hydroxyapatite ($Ca_{10}(PO_4)_6(OH)_2$), octacalcium phosphate ($Ca_8H_2(PO_4)_6 \cdot 5H_2O$), and amorphous calcium phosphate ($Ca_3(PO_4)_2 \cdot nH_2O$). Of these examples, hydroxyapatite and octacalcium phosphate useful for cell culture are preferable, and a more preferable example is hydroxyapatite having high biocompatibility and high cell affinity. However, according to the present invention, cells can be sufficiently cultured even when the substratum comprises a substrate of an inorganic material (particularly, $SiO_2$) that is not coated with the above film. In this case, the substrate preferably comprises a pure inorganic material (particularly, $SiO_2$) forming an amorphous structure (as measured by XRD).

The thickness of the porous $SiO_2$ film or the calcium phosphate compound film preferably ranges from 1 nm to 200 nm, more preferably 5 nm to 170 nm, further preferably 10 nm to 160 nm, and most preferably 40 nm to 150 nm. Because of the film thickness ranging from 1 nm to 200 nm, it is unlikely that the surface shape of the substrate of the cell culture substratum significantly differs from the concavo-convex structures of the culturing surface even when coated. Hence, the concavo-convex structure of the cell culture substratum can be easily formed as desired. From the same viewpoint, the above film is preferably conformally formed in the concavo-convex structures. Furthermore, the porous $SiO_2$ film or calcium phosphate compound film can also be used for fine adjustment of the average length of the contour curve elements of the concavo-convex structures, aspect ratios, the watershed heights of contour curves, and the roughness value of the concavo-convex structures. For example, fine adjustment is possible such that as the film thickness increases, the average length of contour curve elements is lowered without significantly changing the watershed height of the contour curve. Regarding a method for measuring film thickness, a porous $SiO_2$ film or a calcium phosphate compound film is formed on the surface of the cell culture substratum, forming a film-free region and a film region (region with a film), the boundary between the film-free region and the film region is scanned using an atomic force microscope or a stylus-type surface roughness measuring instrument, for example, and thus the film thickness can be measured. An example of a method for forming a film-free region is a method that involves putting a substance inhibiting film formation (for example, a chemical resistant polyimide tape) on a portion of the substrate surface in advance. Further, to measure the film thickness of an intact cell culture substratum (non-destructive), the surface of a sample is subjected to X-ray irradiation at an extremely shallow angle (for example, 0.1° to 5.0°) by X-ray reflectivity (for example, Rigaku Corporation, Smart Lab 9 kW), the X-ray intensity profile of X-rays reflected at an angle which mirrors the incident light angle is measured, the result is compared with the known simulation results of the porous $SiO_2$ film or the calcium phosphate compound film to optimize parameters, and thus the film thickness can be measured. In addition, a film cross section is cut from a cell culture substratum using a focused ion beam processor, the film cross section is observed using a high-resolution transmission electron microscope (for example, Hitachi High-Technologies Corporation: HT7700), and then the film thickness can be actually measured.

When the visible-light transmission of the cell culture substratum is less than 70%, the light transmission performance and the observation sensitivity are low, and thus this is problematic for use in cell observation, and the like. Therefore, in the embodiments of the present invention, the visible-light transmission of the cell culture substratum is preferably 70% or more. Such visible-light transmission realizes the cell culture substratum having excellent transparency, and facilitates successful cell observation under an optical microscope. More preferably the visible-light transmission is 80% or more, and further preferably the visible-light transmission is 90% or more. Moreover, a typical example of a conventional cell culture substratum having visible-light transmission of less than 70% is a substratum produced by coating a polystyrene culture dish with an inorganic material. For example, in the case of a substratum produced by coating a polystyrene cell culture dish with calcium phosphate nanocrystal having high cell affinity by a casting method, the visible-light transmission is about 64% and thus such a substratum is problematic for use in optical observation. Furthermore, the casting method is unable to control the arrangement of particles, results in the formation of a relatively rough film structure due to the agglomerates of particles, and causes irregular reflection of light. For that reason, such conventional substratum is problematic for use in cell observation and the like. The conventional substratum is also problematic in terms of ultraviolet rays absorption by polystyrene, however, the cell culture substratum of the present embodiments causes no such problems since materials absorbing ultraviolet rays such as polystyrene are not used in the substratum.

(Method for Forming Concavo-Convex Structures)

A method for forming concavo-convex structures on the culturing surface of the cell culture substratum is not particularly limited, and known grinding-polishing methods can be used. As an example, a method for forming concavo-convex structures on a culturing surface via grinding and polishing when quartz glass (silica) is used as the cell culture substratum, is as described below.

<Grinding Step>

A grinding step is generally performed by a free abrasive grain method that involves holding a plate-shaped work piece between the upper and the lower surface plates, and then rotating the surface plates and the workpiece for relative displacement, while feeding a polishing liquid (polishing slurry) containing free abrasive grains, or a fixed abrasive method that involves pelletizing diamond fines with a bond such as a resin, metal, or vitrified bond, arranging the multiple pellets on a surface plate, and then rotating the surface plate and the workpiece for relative displacement, while feeding a grinding fluid (coolant) to the surface plate. Moreover, grinding may also be performed using a diamond pad. When a quartz glass substrate subjected to the grinding step, defects such as significant waviness, chips, and cracks are almost completely removed from the substrate.

<Washing Step after Grinding>

On the surface of a quartz glass substrate subjected to the grinding step, a grinding fluid and quartz glass powder can remain. Accordingly, a washing step is preferably provided. In the washing step, various washing methods can be employed. For example, a quartz glass substrate may be subjected to alkali washing alone, or, acid washing followed by alkali washing, or, acid washing alone.

<Polishing Step>

A polishing step is a step for polishing the surface of a glass substrate, so that surface roughness (concavo-convex structure) required in the end can be efficiently achieved. A polishing method to be employed for this step is not particularly limited. Polishing can be performed in a double face polishing machine using a polishing pad and a polishing liquid. Note that concavo-convex structures are essential in the present embodiments, and thus a so-called specular surface polishing step is preferably not performed.

As a polishing pad, in order to easily achieve the surface roughness (concavo-convex structure) required in the end, a hard pad is preferably used, and for example, urethane foam is preferably used. As a polishing liquid, a liquid prepared by using cerium oxide having an average particle diameter between 0.6 μm and 2.5 μm as abrasive grains (polishing material), and dispersing the abrasive grains into water to form a slurry is preferably used. The mixing ratio of water and abrasive grains ranges from about 1:9 to 3:7.

<Washing Step after Polishing>

After the polishing step, a step of washing a quartz glass substrate is preferably employed. A washing method is not particularly limited, and any washing method may be employed, as long as the surface of a quartz glass substrate after the polishing step can be washed clean. The washed quartz glass substrate is subjected to ultrasonic washing and a drying step, as necessary. The drying step is a step for drying the surface of a quartz glass substrate after removal of the washing solution remaining on the surface of the quartz glass substrate using isopropylalcohol (IPA) or the like. For example, a quartz glass substrate after scrubbing is subjected to 2 minutes of a water rinsing and washing step, and then residues of the washing solution are removed. Subsequently, an IPA washing step is performed for 2 minutes, so as to remove water remaining on the surface of the quartz glass substrate with IPA. Finally, an IPA steam drying step is performed for 2 minutes, followed by drying while removing liquid IPA adhering to the surface of the quartz glass substrate with IPA steam. A step for drying a quartz glass substrate is not particularly limited, and for example, a drying method known as a method for drying a quartz glass substrate, such as spin drying, and air knife drying can be employed.

(Method for Producing Cell-Containing Material)

The method for producing a cell-containing material of the present embodiments comprises a step of applying cells to and culturing cells in the concavo-convex structures of the cell culture substratum. Through application of cells to the concavo-convex structures, cell-containing materials such as cellular tissue and biological tissue enabling highly activated cell culturing and being excellent in adhesiveness to the substratum can be produced.

In the method for producing a cell-containing material, when cells are cultured using a cell culture substratum comprising polystyrene, and the culture time required for the cell density to reach 90% of the culturing surface of the cell culture substratum comprising polystyrene is designated as 1T, cells are preferably cultured using the cell culture substratum of the present embodiments and the culture time between ½T and ⅔T. For example, unlike a case in which the culture time required for the cell density to reach 90% of the culturing surface of the cell culture substratum comprising polystyrene is 24 hours, the use of the cell culture substratum of the present embodiments makes it possible to culture cells within a culture time of as short as 12 to 16 hours, which is required for the cell density to reach 90% of the culturing surface of the cell culture substratum of the present embodiments.

(Method for Producing Cell Culture Substratum for Recycling)

According to the present embodiments, a method for producing a cell culture substratum for recycling by autoclaving the cell culture substratum can be provided. A conventional polystyrene dish can be sterilized with a gamma ray. However, a gamma ray sterilizer requires a large-scale facility because of radiation management, polystyrene dishes used for culturing cells have been often discarded after use. In contrast, the cell culture substratum of the present embodiments having a substrate composed of an inorganic material, and thus can be sterilized by autoclaving. Hence, for example, a cell culture substratum immediately after the use thereof in a laboratory can be immediately sterilized and then a cell culture substratum for recycling can be produced.

Conditions for autoclaving differ depending on materials to be used for the cell culture substratum. For example, when a quartz glass (silica) substrate is used, 20 minutes of autoclaving is performed at a temperature between 100° C. and 150° C., pressure between 0.10 MPa and 0.5 MPa, heat time between 1 minute and 30 minutes, and preferably at a temperature of 121° C. and saturated aqueous vapor pressure of 0.20 MPa.

In the production method, proteins on the autoclaved cell culture substratum are preferably removed. A maintenance fluid is repeatedly used for treatment, facilitating the removal of proteins that are residual substances on the cell culture substratum.

(Maintenance Fluid)

A maintenance fluid for the cell culture substratum of the present embodiments is used for removing cell adhesive proteins secreted by cells and extracellular matrix (for example, fibrinogen), which are residual substances on the cell culture substratum, and contains proteolytic components. As a maintenance fluid, for example, ethanol, phosphate-buffered saline (PBS), fetal bovine serum (FBS), cell culture solution (αMEM)-containing FBS/αMEM medium, sodium dodecyl sulfate (SDS) or the like is used and then weakly bound proteins and the like can be removed. Subsequently, a solution in which the weight ratio of ultrapure water:ammonia water:hydrogen peroxide water is 5:1:1, 1N hydrochloric acid, or the like is used and then strongly bound proteins and the like can be degraded and removed. Finally, the substratum is repeatedly rinsed with ultrapure water, and thus the clean surface can be obtained.

(Method for Observing Cells)

The cell observation method of the present embodiments is a method for optically observing cells on the cell culture substratum. Conventional polystyrene dishes reflect light, and thus optical observation has been difficult. Particularly, upon irradiation with ultraviolet rays having wavelengths ranging from 200 nm to 400 nm, fluorescence is emitted from polystyrene, and thus this is unsuitable for observation under ultraviolet light. In contrast, the cell culture substratum of the present embodiments contains no ultraviolet rays-absorbing material such as polystyrene used therein, and has excellent transparency and visible light transmittance, thereby facilitating optical microscopic observation or the like of cells on the cell culture substratum.

EXAMPLES

Specific examples of the present invention are as described below. Further, the present invention is not interpreted as being limited by these examples.

Example 1

Both surfaces of a quartz glass substrate made of silica were ground using a double-sided grinding machine (HAMAI Co., Ltd., 4-way lapping machine). Grinding was performed using zirconia-based alumina (AZ) fines (HEISEI SANKEI Co., Ltd.) as abrasive grains at a load between 60 g/cm$^2$ and 90 g/cm$^2$, with a platen rotation number between 20 rpm and 50 rpm. The thus ground both surfaces of the quartz glass substrate were polished using a double face polishing machine (HAMAI Co., Ltd., 4-Way Polishing machine). Polishing was performed using a urethane foam pad as a polishing pad, and MIREK E (MITSUI MINING & SMELTING Co., Ltd.) as abrasive grains at a load between 60 g/cm$^2$ and 100 g/cm$^2$ with a platen rotation number between 20 rpm and 50 rpm. Therefore, a cell culture substratum comprising a silica substrate was produced.

Example 2

(Method for Producing Cell Culture Substratum Comprising Silica Substrate Coated with Porous Silica Film)

Hexadecyltrimethylammonium chloride (524 mg) (CTAC) was added to 1.4 ml of water and then dispersed by stirring, thereby obtaining solution A. Next, 0.472 ml of water and 0.1 ml of 0.1 N—HCl were added to 1.94 ml of tetramethoxysilane (TMOS), and then the mixture was stirred at 30° C. for 60 minutes, thereby obtaining solution B. Solution A and solution B were mixed so that the molar ratio of TMOS/CTAC was 8, and then 0.1 ml of 1 N—HCl was added, thereby obtaining mixed solution C. Mixed solution C was stirred at room temperature (20° C.) for 15 minutes, and then the silica substrate (12.5 mm×25 mm) of Example 1 having convexo-concave shapes on the culturing surface was subjected to spin coating under conditions of 6000 rpm and 10 seconds. The silica substrate coated with mixed solution C was heated at 60° C. for 18 hours, thereby forming a CTAC/TMOS composite film. Furthermore, the silica substrate with the thus formed composite film was fired at 450° C. for 6 hours. Therefore, a cell culture substratum comprising the silica substrate coated with the porous silica film was produced. The porous silica film had a film thickness of 150 nm. A method for measuring film thickness was performed by putting a chemical resistant polyimide tape (registered trade name: kapton) on parts of the substrate surface in advance, stripping the polyimide tape at a stage before firing after deposition, firing the resultant to obtain a partially deposited substratum, scanning the boundaries between film-free regions (where the tape was put on) and regions with films (where no tape was put on); that is, the surface of this sample using a diamond probe of a stylus-type surface roughness measuring instrument (ULVAC Inc., DEKTACK3ST), obtaining height profiles under conditions of measurement distance: 100 μm, scanning speed: 50s, data points: 8000 points, and probe pressure: 3 mg, and then averaging values at 5 positions to calculate the film thickness.

Example 3

(Method for Producing Cell Culture Substratum Comprising Silica Substrate Coated with Calcium Phosphate)

Water (700 ml) was added to a 1000-ml beaker, and then 11.9850 g of NaCl, 0.525 g of NaHCO$_3$, 0.336 g of KCl, 0.342 g of K$_2$HPO$_4$/3H$_2$O, 0.4575 g of MgCl/6H$_2$O, 57 ml of 1 N—HCl, 0.417 g of CaCl$_2$), 0.1065 g of Na$_2$SO$_4$, 9.0855 g of Na$_2$C(CH$_2$OH)$_3$ were added, followed by stirring at 36.5° C. (stirring was continued until the silica substrate was immersed). Next, the pH of the solution in the beaker was measured, HCl was added so that the pH was 7.4. Subsequently, the solution was transferred to a 1000-ml volumetric flask, so that an apatite coating solution (1.5 SBF) was obtained. The silica substrate (12.5 mm×25 mm) of Example 1 was immersed in 1.5 SBF (2 ml) at 36.5° C., and then left to stand for 35 hours. Subsequently, the silica substrate was washed with ultrapure water, and then fired at 550° C. for 3 hours. Therefore, a cell culture substratum comprising the silica substrate coated with the calcium phosphate film was produced. The calcium phosphate film had a film thickness of 40 nm. A method for measuring film thickness was performed in a manner similar to that in Example 2, by putting a chemical resistant polyimide tape (registered trade name: kapton) on parts of the substrate in advance, stripping the polyimide tape at a stage before firing after deposition, firing the resultant to obtain a partially deposited substratum, and then measuring the boundaries between film-free regions (where the tape was put on) and regions with films (where no tape was put on) using an atomic force microscope (SII NanoTechnology Inc., Probe station name: NanoNavi IIs/Unit name: Nanocute). Specifically, with the use of a cantilever (Model: Micro Cantilever SI-DF40, spring constant: 26 N/m, resonance frequency: 294 Hz) in which a probe made of silicon nitride was mounted, the height at each point was imaged under conditions of measurement mode: dynamic force mode, scanning range: 10 μm×10 μm, scanning frequency: 1.00 Hz, X direction data points: 256 points, and Y direction data points: 256 points. Here, the "height" refers to a difference between each measurement point and the lowest height among the measurement points. The values of height profiles at 5 positions of the cross section of an arbitrary image were averaged to calculate the film thickness.

The above SBF is a pseudo body fluid having artificially reproduced inorganic ion concentrations of human blood plasma, and the ion concentrations of the 1.5 SBF (mM) were Na$^+$: 213.0, K$^+$: 7.5, Mg$^{2+}$: 2.25, Ca$^{2+}$: 3.75, Cl$^-$: 222.0, HCO$_3^-$: 6.3, HPO$_4^{2-}$: 1.5, and SO$_4^{2-}$: 0.75.

Comparative Examples 1 to 2

A cell culture substratum comprising a commercial boron-containing silicate glass substrate (Matsunami Glass Ind., Ltd.) was designated as Comparative example 1, and a cell culture substratum comprising a polystyrene dish (Corning International Corporation., USA) was designated as Comparative example 2.

(Atom Composition Analysis of Substrate Surface)

Figure 2B:
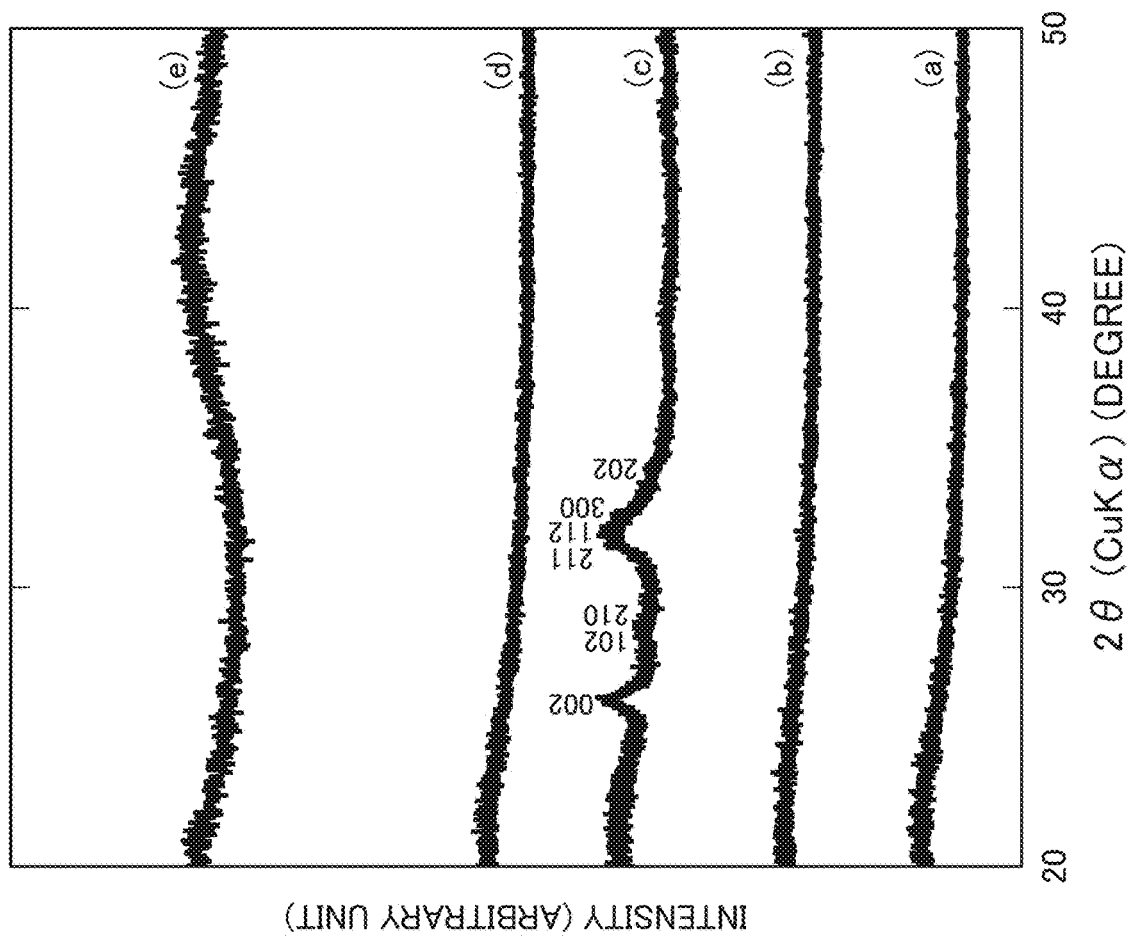
FIG. 2A and FIG. 2B show X-ray diffraction patterns indicating the crystallinity of the surfaces of the cell culture substrata of Examples 1 to 3 and Comparative examples 1 and 2.
Figure 2A:
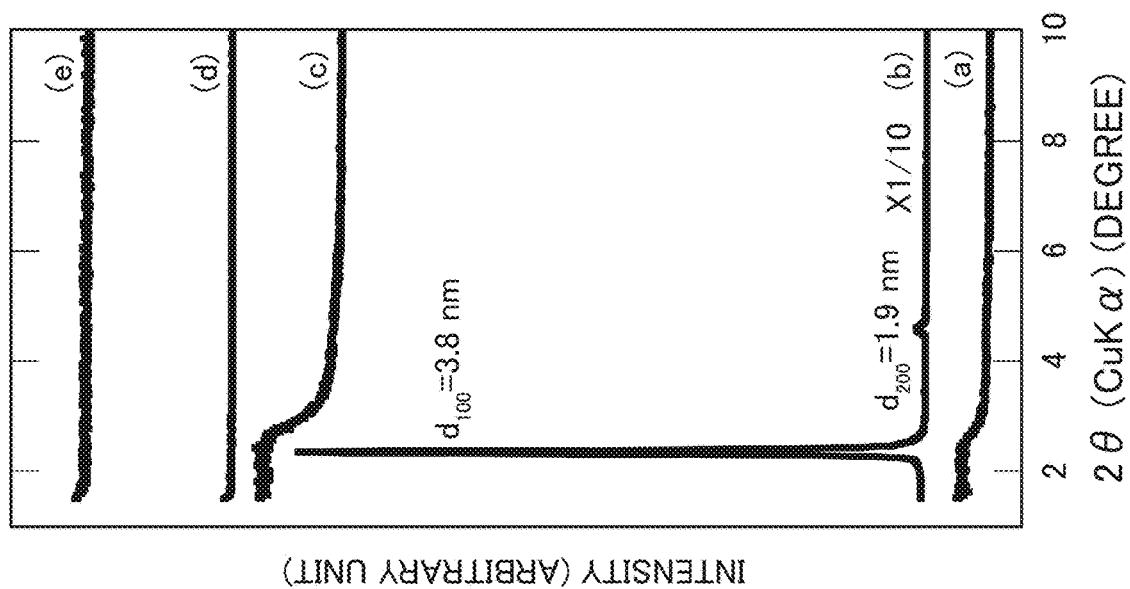

The substrata of Examples 1 to 3 and Comparative examples 1 and 2 were measured for the surface atom compositions by fluorescent X-ray analysis. Moreover, the average transmittance of visible light (400 nm to 800 nm) was measured. Light transmittance was measured using a UV-visible spectrophotometer V-750 (JASCO Corporation) at every 1-nm wavelength of wavelengths ranging from 400 nm to 800 nm. The baseline is determined to be air and the proportion of the light intensity of light that had transmitted among the light intensity of light incident into a substratum and a film was designated as transmittance. All values of light transmittance at each wavelength were averaged, so that the average transmittance in the visible light region was calculated. Measurement results are shown in Table 1.

high-angle region. In FIG. 2A and FIG. 2B, (a) to (c) denote Examples 1 to 3, respectively, and (d) to (e) denote Comparative examples 1 and 2, respectively. As shown in FIG. 2A, in measurement of the low-angle region, a high-intensity peak was observed only for pattern (b). The measurement results demonstrate that the silica film with which the silica substrate of Example 2 was coated had a regular nanoscale micropore structure. Furthermore, in measurement of the high-angle region of FIG. 2B, a peak was observed only for pattern (c). The measurement results indicate Ca and P of the calcium phosphate film, with which the silica substrate of Example 3 was coated.

(Observation of Concavo-Convex Structure)

The substrata of Examples 1 to 3 and Comparative examples 1 and 2 were observed for ultrafine concavo-convex structures of the culturing surfaces using an atomic force microscope. FIG. 3A to FIG. 3E show atomic force microscopic images, in which (a) to (c) denote Examples 1 to 3, respectively, and (d) and (e) denote Comparative examples 1 and 2, respectively. Moreover, the measurement range for the images of FIG. 3A to FIG. 3E was 1 μm$^2$, and the height in the contour curve described below is shown on the right side of each image.

FIG. 3A shows that on the surface of the substratum of Example 1, straight-line-shaped groove structures; that are multiple concavo-convex structures were formed in parallel, and Rrms value was 0.38 nm. Furthermore, FIG. 3B shows that on the surface of the substratum of Example 2, flaky concavo-convex structures were formed and Rrms value was 1.43 nm. FIG. 3C shows that on the surface of the substratum of Example 3, flaky concavo-convex structures with straight-line-shaped grooves were formed, and Rrms value was 1.21 nm. On the other hand, the shape of the surface of the substratum of Comparative example 1 was indefinite shape, and Rrms value was 2.18 nm (FIG. 3D). On the surface of the substratum of Comparative example 2, random fibrous tissue was observed, and Rrms value was 1.87 nm (FIG. 3E).

Furthermore, the substrata of Examples 1 to 3 and Comparative examples 1 and 2 were subjected to measurement of the surface shape. Specifically, in accordance with JISB0601 (2013), and JISR1683 (2014), an atomic force microscope (Probe station name: NanoNavi IIs/Unit name: Nanocute, SII NanoTechnology Inc.) was used, and a cantilever (model: Micro Cantilever SI-DF40, spring constant: 26 N/m,

TABLE 1

| | Elemental composition (mol %) | | | | | | | | | | | Average transmittance of visible light (%) |
|---|---|---|---|---|---|---|---|---|---|---|---|---|
| | Ca | Si | O | P | Na | Al | K | Ti | B | Zr | Sb | |
| Example 1 | 0.00 | 32.3 | 67.7 | 0.00 | 0.00 | 0.00 | 0.00 | 0.00 | 0.00 | 0.00 | 0.00 | 94 |
| Example 2 | 0.00 | 24.2 | 75.8 | 0.00 | 0.00 | 0.00 | 0.00 | 0.00 | 0.00 | 0.00 | 0.00 | 88 |
| Example 3 | 2.15 | 0.00 | 90.2 | 5.58 | 0.00 | 0.00 | 0.14 | 0.00 | 0.00 | 0.00 | 0.00 | 79 |
| Comparative Example 1 | 0.00 | 20.5 | 62.8 | 0.00 | 3.44 | 1.65 | 2.80 | 1.07 | 7.74 | 0.002 | 0.009 | 92 |
| Comparative Example 2 | 0.00 | 0.00 | 0.00 | 0.00 | 0.00 | 0.00 | 0.00 | 0.00 | 0.00 | 0.00 | 0.00 | 90 |

(Measurement of X-Ray Diffraction Pattern)

X-ray diffraction patterns of the substrata of Examples 1 to 3 and Comparative examples 1 and 2 were measured. Measurement results are shown in FIG. 2A and FIG. 2B. FIG. 2A shows X-ray diffraction patterns in the low-angle region, and FIG. 2B shows X-ray diffraction patterns in the resonance frequency: 294 Hz) mounted with a probe made of silicon nitride was used. Measurement conditions are as follows. Measurement mode: dynamic force mode
Scanning range: 1 μm×1 μm
Scanning frequency: 1.00 Hz
X direction data points: 256 points Y direction data points: 256 points
Low-pass filter value: 1 nm
High-pass filter value: 150 nm Contour curves obtained by measurement using the atomic force microscope were analyzed using analysis software (product name: NanoNavi II/IIs, SII NanoTechnology Inc.), thereby calculating the average lengths of contour curve elements of the concavo-convex structures, watershed heights, and aspect ratios (see Table 2). Note that the average line is a line that is parallel with a straight line and indicates a height cumulative relative frequency distribution in the contour curve of 50%, when a curve representing long-wavelength components that are blocked by the high-pass contour curve filter is converted to the straight line by the least square method. The watershed height is, under a condition where an upper end line indicating a height cumulative relative frequency distribution of 100% in the contour curve and a lower end line indicating a height cumulative relative frequency distribution of 0% are inverted for horizontal correction, the average distance between the lowest point of valleys after inversion and the lower end line in the contour curve measured by the watershed method. Measurement by the watershed method was automatically processed by a program to which Vincent-Soille's algorithm (L. Vincent, P. Solle "Watersheds in Digital Spaces: An Efficient Algorithm Based on Immersion Simulations", IEEE Transactions on Pattern Analysis and Machine Intelligence, 13(6), 583 (1991).) had been applied. The aspect ratio was found by calculating average length W1 of the contour curve elements of the concavo-convex structures in direction X and average length W2 of the contour curve elements of the concavo-convex structure in direction Y perpendicular to direction X, dividing the value of W1 or W2 higher than the other by the value of W1 or W2 lower than the other, and then averaging the result.

TABLE 2

| | Average length of contour curve elements ± standard deviation (nm) | Watershed height (nm) | Average aspect ratio ± standard deviation |
|---|---|---|---|
| Example 1 | 134 ± 39 | 3.71 | 1.92 ± 0.67 |
| Example 2 | 34 ± 5 | 4.82 | 1.24 ± 0.11 |
| Example 3 | 79 ± 18 | 3.76 | 1.36 ± 0.26 |
| Comparative Example 1 | 298 ± 89 | 10.71 | 2.00 ± 0.43 |
| Comparative Example 2 | 243 ± 34 | 8.15 | 2.02 ± 0.44 |

(Measurement of Amount of Protein Adsorbed)

In an incubator (5%-$CO_2$, 37° C.), the substrata of Examples 1 to 3 and Comparative examples 1 and 2 were subjected to 1 hour of protein adsorption. After removed, the substrata were washed with phosphate-buffered saline (PBS), 2 ml of 1 wt %-sodium dodecyl sulfate (SDS) solution was added, and then proteins adsorbed onto the substrata were removed for 1 hour on a shaker (100 rpm). With the use of the solutions subjected to removal, the amounts of proteins adsorbed were measured by colorimetry. Specifically, reagent "Quanti Pro Buffer QA" and reagent "Quanti Pro BCA QB Copper (II) sulfate solution" were added to the solution subjected to removal, and then the solution was left to stand in the incubator for 24 hours. Subsequently, absorbance was measured by UV spectrum measurement so as to find the adsorption amounts.

Colorimetry (BCA method) employs a 2-stage reaction. Specifically, firstly, peptide bonds of proteins cause $Cu^{2+}$ ions to be reduced to $Cu^+$, and secondly, as shown in the following structural formula, 2 molecules of bicinchoninic acid (BCA) cause the chelate-coordination of $Cu^+$ ions, generating a violet product ($Cu(I)(BCA)_2$ complex). The coloring intensity of violet depends on protein concentration. Hence, absorbance at 562 nm is measured and then protein concentration can be quantified.

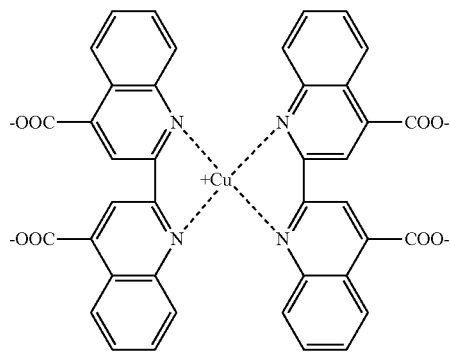

Results of measuring the amounts of proteins adsorbed are shown in FIG. 4. As shown in FIG. 4, whereas the amount of albumin adsorbed was higher in the substrata of Comparative examples 1 and 2 than in the substrata of Examples 1 to 3, the amount of fibrinogen adsorbed was higher in the substrata of Examples 1 to 3 than in the substrata of Comparative examples 1 and 2. Since fibrinogen, the adsorption amount thereof was higher in the substrata of Examples 1 to 3, is a cell adhesive protein, and thus the substrata of Examples 1 to 3 are excellent in cell adhesiveness. On the other hand, albumin, the adsorption amount thereof was higher in the substrata of Comparative examples 1 and 2 is a cell adhesion-inhibiting protein, and thus the substrata of Comparative examples 1 and 2 are inferior in cell adhesiveness to the others.

(Evaluation of Cell Viability and Adhesion Area)

The substrata of Examples 1 to 3 and Comparative examples 1 and 2 were sterilized and washed. Specifically, sterilization and washing were performed using 50 vol %, 70 vol % and 90 vol % ethanol, three times each, PBS three times, and 10 vol % FBS/aMEM medium containing fetal bovine serum (FBS) and cell culture solution (αMEM) three times.

Osteoblast-like cells (MC3T3-E1) were cultured in 10 vol % FBS/αMEM medium for 1 week. Cells were cultured under conditions of 37° C., $CO_2$ concentration of 5%, and relative humidity of 99%. After culturing, the substrata were washed with PBS, trypsin/ethylenediamine tetraacetic acid (EDTA) and PBS, so as to wash off cells that had not adhered to the substrata. After washing, 10 vol % FBS/αMEM medium was added.

Osteoblast-like cells, the thus cultured cell density of which was 5000 cells/$cm^2$, were seeded on the substrata of Examples 1 to 3 and Comparative examples 1 and 2. Cells were cultured under conditions of 37° C., $CO_2$ concentration of 5%, and relative humidity of 99%, and the viability and the cell area (cell adhesion area) of cultured cells were measured at 5 hours, 22 hours, 55 hours and 72 hours later. The cell viability was measured by an MTT assay method. The MTT assay method involves: extracting using dimethyl sulfoxide a formazan dye generated as a result of reduction of MTT [3-(4,5-dimethyl-thiazol-2-yl)-2,5-diphenyltetrazolium bromide] incorporated into cells by intracellular mitochondrial dehydrogenase (succinate dehydrogenase); determining the absorbance of the formazan dye solution at a wavelength of 570 nm by colorimetry; and then measuring the cell viability. Absorbance was measured at a wavelength of 570 nm at each culture time using a UV-visible spectrophotometer V-750 (JASCO Corporation), and 10 vol % FBS/αMEM medium as the background. Here, the term "cell viability (%)" refers to the relative proportion of the absorbance at each culture time, which is represented by % relative to the highest absorbance in the MTT assay method in the Examples and Comparative examples designated as 100%. Moreover, the term "cell area" refers to the area of one cell adhering to a culturing surface, and the average of the areas of 100 cells imaged at each culture time by an inverted routine microscope CKX41 (Olympus Corporation).

Figure 5:
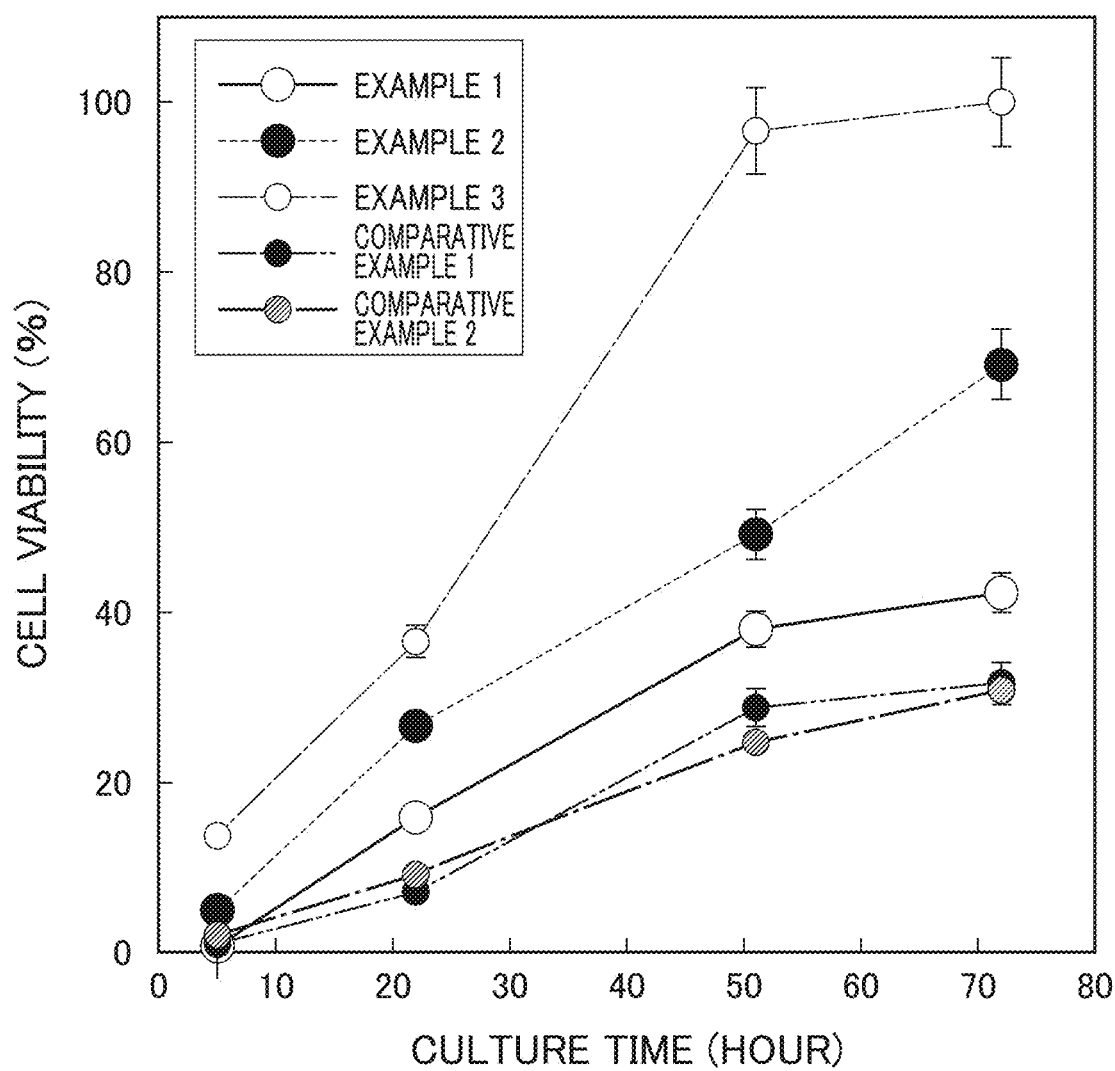
FIG. 5 is a graph showing the relationship between the cell culture time and the cell viability in the cell culture substrata of Examples 1 to 3 and Comparative examples 1 and 2.

FIG. 5 is a graph showing the relationship between the cell culture time and cell viability of the substrata of Examples 1 to 3 and Comparative examples 1 and 2. As shown in FIG. 5, as the cell culture time elapsed, cells proliferated and tended to exhibit improved cell viability. In Examples 1 to 3, the cell viability was higher than 40% when the cell culture time was 72 hours, indicating high cell survival even after lengthy culturing. Particularly, Example 3 provided with concavo-convex structures coated with the calcium phosphate film exhibited the cell viability of nearly 100% when cell culture time was 72 hours. Furthermore, Comparative example 1 tended to exhibit low cell viability because of its culturing surface containing $B_2O_3$.

Figure 6:
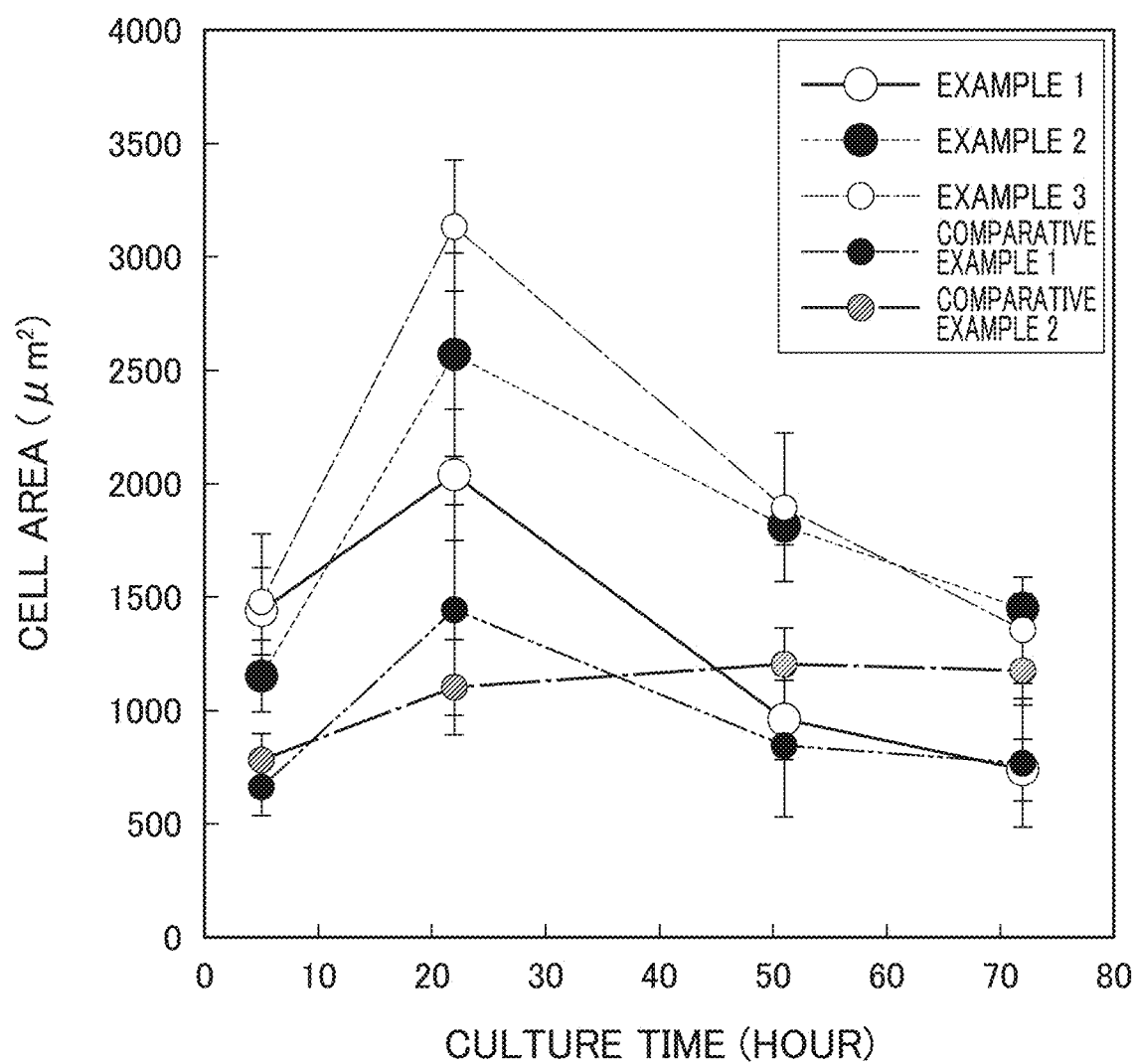
FIG. 6 is a graph showing the relationship between the cell culture time and the cell area in the cell culture substrata of Examples 1 to 3 and Comparative examples 1 and 2.

FIG. 6 is a graph showing the relationship between cell culture times and cell areas in the substrata of Examples 1 to 3 and Comparative examples 1 and 2. As shown in FIG. 6, Examples 1 to 3 and Comparative example 1 exhibited a tendency such that the cell area was the highest when the culture time was 22 hours, while the cell area decreased when the culture time reached 55 hours, and then 72 hours. This is because when cells excessively proliferate, spaces between cells decrease and cells become smaller in size. Examples 1 to 3 exhibited the cell area of higher than 2000 $\mu m^2$ when the cell culture time was 22 hours, demonstrating their excellent cell adhesiveness. Particularly, Example 3 provided with the concavo-convex structures coated with the calcium phosphate film exhibited the cell area of higher than 3000 $\mu m^2$ when the cell culture time was 22 hours.

EXPLANATION OF REFERENCE NUMERALS

M . . . Contour curve of concavo-convex structure
TA . . . Average line indicating height cumulative relative frequency distribution of 50%
$P_1$ . . . $1^{st}$ peak
$P_2$ . . . $2^{nd}$ peak
Q . . . Valley
A . . . Starting point of $1^{st}$ peak $P_1$
B . . . End point of valley Q

The invention claimed is:

1. A cell culture substratum provided with a substrate composed of an inorganic material comprising $SiO_2$, wherein
the cell culture substratum has multiple concavo-convex structures on a culturing surface thereof,
when the concavo-convex structures are measured with an atomic force microscope,
the average length of the contour curve elements of the concavo-convex structures ranges from 1 nm to 170 nm as measured in at least one direction.

2. The cell culture substratum according to claim 1, wherein the watershed height of the contour curve ranges from 0.1 nm to 8 nm.

3. The cell culture substratum according to claim 1, wherein the aspect ratio of average length W1 of contour curve elements of the concavo-convex structures in direction X to average length W2 of contour curve elements of the concavo-convex structures in direction Y perpendicular to direction X is 1.95 or less.

4. The cell culture substratum according to claim 1, wherein the culturing surface forms the concavo-convex structures coated with a porous $SiO_2$ film.

5. The cell culture substratum according to claim 1, wherein the culturing surface forms the concavo-convex structures further coated with a calcium phosphate compound film.

6. The cell culture substratum according to claim 5, wherein the thickness of the porous $SiO_2$ film or the calcium phosphate compound film ranges from 1 nm to 200 nm.

7. The cell culture substratum according to claim 1, wherein the culturing surface does not contain $B_2O_3$.

8. The cell culture substratum according to claim 1, wherein the visible-light transmission is 70% or more.

9. The cell culture substratum according to claim 1, wherein the concavo-convex structures are grooved, porous or flaky.

10. A method for producing a cell-containing material, having a step of culturing cells using the cell culture substratum according to claim 1.

11. A method for producing a cell-containing material, comprising culturing cells using a cell culture substratum comprising polystyrene, wherein when the culture time, required for the cell density to reach 90% of the culturing surface of the cell culture substratum comprising polystyrene is designated as T, cells are cultured with the culture time between ½T and ⅔T using the cell culture substratum according to claim 1.

12. A method for producing a cell culture substratum, comprising autoclaving the cell culture substratum according to claim 1, and then producing the cell culture substratum for recycling.

13. A method for observing cells, comprising optically observing cells on the cell culture substratum according to claim 1.

14. A method for removing a cell adhesive protein on the cell culture substratum according to claim 1, the method comprising using a maintenance fluid containing a component for degrading the cell adhesive protein.

* * * * *